United States Patent [19]

Felder et al.

[11] Patent Number: 4,503,252

[45] Date of Patent: Mar. 5, 1985

[54] PROCESS FOR THE PREPARATION OF SERINOL AND OF SERINOL DERIVATIVES, AND PRODUCTS OBTAINED THEREFROM

[75] Inventors: Ernst Felder, Riva S. Vitale, Switzerland; Sergio Bianchi, Milan, Italy; Heinrich Bollinger, Beringen, Switzerland

[73] Assignee: Eprova Aktiengesellschaft, Schaffhausen, Switzerland

[21] Appl. No.: 441,777

[22] Filed: Nov. 15, 1982

Related U.S. Application Data

[63] Continuation of Ser. No. 183,860, Sep. 3, 1980, abandoned.

[30] Foreign Application Priority Data

Sep. 10, 1979 [CH] Switzerland .................. 8182/79

[51] Int. Cl.$^3$ .................. C07C 85/04; C07C 85/24
[52] U.S. Cl. .................. 564/474; 544/401
[58] Field of Search .................. 564/474; 544/401

[56] References Cited

U.S. PATENT DOCUMENTS

| | | | |
|---|---|---|---|
| 2,490,385 | 12/1949 | Sweet | 564/474 |
| 2,628,254 | 2/1953 | Copenhaver | 564/474 |
| 2,709,169 | 5/1959 | Morren | 544/401 |

FOREIGN PATENT DOCUMENTS 2742981  3/1979  Fed. Rep. of Germany ...... 564/474

OTHER PUBLICATIONS

Fairbourne et al., "Chem. Abs.", 25, p. 2692.
Cram et al., "Organic Chemistry", 2nd Ed., McGraw-Hill, N.Y. (1964) pp. 259–260.
Lagenbeck et al., "Chem. Abs.", 51, 1957, p. 17743f.
Schach, "Chem. Abs.", 54, 1960, p. 9771e.
Schipper et al., "Chem. Abs.", 56, 1962, p. 8709c.
Morrison et al., "Organic Chemistry", 3rd Ed., Allyn & Bacon, Inc., Boston (1973) p. 559.

*Primary Examiner*—Paul F. Shaver
*Attorney, Agent, or Firm*—Toren, McGeady and Stanger

[57] ABSTRACT

A method for the synthesis of serinol and serinol derivatives substituted at the nitrogen atoms by reacting a lower 1,3-dialkoxy-isopropyl halide with ammonia or an amine to form a 1,3-dialkoxy-isopropylamine and then removing the ether groups by heating with a hydrogen halide acid. The method allows the production of serinol and serinol derivatives using inexpensive starting materials in a simple manner and obtaining a high purity product which is free of interfering isomers. Novel compounds obtained by the method which are useful as pharmaceutical intermediates, X-ray contrasting agents and cytostatic or psychopharmacological drugs are also disclosed.

2 Claims, No Drawings

PROCESS FOR THE PREPARATION OF SERINOL AND OF SERINOL DERIVATIVES, AND PRODUCTS OBTAINED THEREFROM

This is a continuation of application Ser. No. 183,860, filed Sept. 3, 1980, now abandoned.

BACKGROUND OF THE INVENTION

1. Field of the Invention

The present invention relates to a novel and very advantageous process for the rational synthesis of serinol on an industrial scale, as well as of serinol derivatives substituted at the nitrogen atom obtained from the process.

2. Description of the Prior Art

Serinol (1,3-dihydroxy-isopropylamine), may be synthesized by the reduction of the oxime of 1,3-dihydroxyacetone. As a result of isomerization, however, a mixture of serinol and 2,3-dihydroxy-propylamine results which is extremely difficult to separate. Serinol is therefore generally synthesized from nitromethane. For this purpose, nitromethane is reacted in an alkaline solution with formaldehyde to form 2-nitro-1,3-propanediol which is then catalytically reduced to serinol. However, undesirable side reactions may also occur in this process. In this connection, reference is made to Schmidt et al, Ber. dtch. chem. Ges., 52, 389, Langenbeck et al, Naturwissenschaften 42, (1955), 389–90; Schipper et al, J. Org. Chem. 26 (1961), 4145–8; Pfeiffer, German Auslegeschrift No. 2,742,981 (Schering A. G.).

This method requires handling the highly explosive nitromethane and the even more dangerous 2-nitro-1,3-propanediol or its sodium salt. Accidents with nitroalkanes have led to such restrictive Government regulations that aliphatic nitro compounds may now be used only in highly safeguarded, far-removed plants, whose equipment and operation is profitable only for large scale products.

As a result, it is difficult to buy serinol in sufficient amounts or to have it synthesized from nitromethane since no one was willing or permitted to take such high risks.

SUMMARY OF THE INVENTION

We have discovered a method that avoids the difficulties described above whereby serinol can be synthesized in a simple manner from very cheap raw materials, in high purity and free from interfering isomers. This is accomplished by reacting epichlorohydrin in a known manner in the presence of strong alkalies with a lower alcohol to form 1,3-dialkoxyisopropanol which is transformed by known methods to the corresponding 1,3-dialkoxy-isopropyl halide. This, in turn, is converted by reaction with ammonia or a primary or secondary amine to form the 1,3-dialkoxy-isopropylamine from which the ether groups are split off by heating with a hydrogen halide acid, hydrochloric acid, hydrobromic acid or hydroiodic acid. Boiling hydrochloric acid suffices to effect the splitting off. The use of hydrochloric acid has the additional advantage that there is hardly any conversion of OH functions into Cl functions in the boiling hydrochloric acid. All synthesis operations can be carried out very easily and produce outstanding yields on an industrial scale.

We have further discovered a series of novel 1,3-dihydroxy-isopropylamines, substituted at the nitrogen, which can be produced by the inventive process. These compounds have the formula (III).

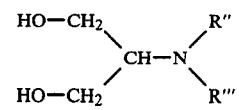

in which
R" represents hydrogen, methyl, ethyl, hydroxyethyl, dihydroxypropyl or, together with R''' and the nitrogen atom, a component of a pyrrolidine or a piperazine ring, and
R''' represents di-, tri-, tetra- or pentahydroxyalkyl with 2 to 6 carbon atoms or, together with R" and the nitrogen atom, one of the aforementioned heterocyclic rings.

These 1,3-dihydroxy-isopropylamines, like serinol itself, are suitable as intermediates for the synthesis of pharmaceutically active materials, for example, of X-ray contrasting materials, cytostatic or psychopharmacological drugs, etc., as well as, in part, for the formation of salts of strong organic acids, for example, of 3,5-substituted 2,4,6-triiodobenzoic acids.

DESCRIPTION OF THE PREFERRED EMBODIMENTS

Lower alcohols, suitable for the reaction with epichlorohydrin, include methanol, ethanol, and propanol.

More particularly, the process of the present invention comprises reacting a lower 1,3-dialkoxy-isopropyl halide which is readily obtainable by known methods from epichlorohydrin via 1,3-dialkoxy-isopropanol with ammonia or an amine of the formula (I)

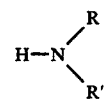

in which
R preferably is hydrogen, methyl, ethyl, hydroxyethyl, dihydroxypropyl, or, together with R' and the nitrogen atom, a component of a pyrrolidine, a piperidine, a morpholine or a piperazine ring, and
R' represents hydrogen, methyl, ethyl or hydroxyalkyl, di-, tri, tetra- or pentahydroxyalkyl with 2 to 6 carbon atoms or, together with R and the nitrogen atom, one of the aforementioned heterocyclic rings,
to produce a 1,3-dialkoxy-isopropylamine or 1,3-dialkoxy-isopropylamine derivative of formula (II)

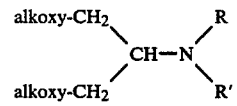

in which alkoxy stands for lower alkoxy residues with 1 to 3 carbon atoms. Thereafter, the ether groups are split off by heating with a hydrogen halide acid.

The preferred process consists of using 1,3-dimethoxy-isopropyl chloride as the intermediate for the inventive synthesis and of effecting the ether splitting with hydrochloric acid.

The simplest industrial process for synthesizing serinol pursuant to the present invention involves reacting 1,3-dimethoxy-isopropyl chloride with excess ammonia and converting the 1,3-dimethoxy-isopropylamine obtained into serinol by boiling under reflux with aqueous hydrochloric acid, the hydrogen chloride being consumed constantly or being periodically replaced in order to accelerate the reaction.

A number of serinol derivatives are known, e.g., 1,3-dihydroxy-2-dimethylamino-propane, 1,3-dihydroxy-2-diethylamino-propane, 1,3-dihydroxy-2-(2'-hydroxyethyl)-amino-propane, 1(N)-(1,3-dihydroxyisopropyl)-piperidine and 4(N)-(1,3-dihydroxyisopropyl)-morpholine.

1,3-dihydroxy-2-dimethylaminopropane was obtained according to the method of Ioffe et al, Zhur. Obshch.Khim. 34(4), 1336–41 (Chemical Abstracts 61, 1964, 1790h) from 2-nitro-1,3-propanediol by hydrogenation in acetic acid in the presence of formalin and Raney nickel in a yield of 42%.

1,3-dihydroxy-2-diethylamino-propnae was synthesized according to the method of M. Ishidate et al, Chem. Pharm. Bull. (Tokyo) 8, 732–7 (1960), (Chemical Abstracts 55, 1961, 18575h) by the reaction of diethyl bromomalonate with diethylamine and reduction of the diethyl aminomalonate obtained with lithium aluminum hydride.

1,3-dihydroxy-2-(2'-hydroxyethyl)-amino-propane was obtained according to the method of Williamson et al, J. Med. Chem. 10 (3), 511 (1967) (Chemical Abstracts 67, 1967, 64368s) from serinol by reaction with ethylene oxide.

Ferretti et al, Tetrahedron Letters 1964, (38–40), 2975–9 (Chemical Abstracts 62, 1965, 1536g) synthesized N-(1,3-dihydroxyisopropyl)-morpholine from N-allyl morpholine by treatment with Ag(BzO)$_2$I and saponification of the dibenzoate obtained.

Typical products of the process of the present invention include: serinol (=1,3-dihydroxy-isopropylamine) as well as certain novel 1,3-dihydroxy-isopropylamine derivatives (as mentioned, compounds (3), (10), (11), (16) and (17) are known):
(1) 1,3-dihydroxy-2-methylamino-propane,
(2) 1,3-dihydroxy-2-ethylamino-propane,
(3) 1,3-dihydroxy-2-(2'-hydroxyethyl)-amino-propane,
(4) 1,3-dihydroxy-2-(2',3'-dihydroxypropyl)-amino-propane,
(5) 1,3-dihydroxy-2-(2',3',4'-trihydroxy-butyl)-aminopropane,
(6) 1,3-dihydroxy-2-[N-methyl-N-(2',3',4',5'-tetrahydroxypentyl)]-amino-propane,
(7) 1,3-dihydroxy-2-[N-methyl-N-(2',3',4',5',6'-pentahydroxyhexyl)]-amino-propane,
(8) N,N-bis-(1,3-dihydroxy-isopropyl)-amine,
(9) 1,3-dihydroxy-2-[tris-(hydroxymethyl)-methyl]-amino-propane,
(10) 1,3-dihydroxy-2-dimethylamino-propane,
(11) 1,3-dihydroxy-2-diethylamino-propane,
(12) 1,3-dihydroxy-2-[N,N-bis-(2-hydroxyethyl)]-amino-propane,
(13) 1,3-dihydroxy-2-[N,N-bis-(2,3-dihydroxypropyl)]-amino-propane,
(14) 1,3-dihydroxy-2-[N,N-bis-(2,3-dihydroxyisopropyl)]-amino-propane,
(15) 1(N)-(1,3-dihydroxyisopropyl)-pyrrolidine,
(16) 1(N)-(1,3-dihydroxyisopropyl)-piperidine,
(17) 4(N)-(1,3-dihydroxyisopropyl)-morpholine,
(18) 1(N)-(1,3-dihydroxyisopropyl)-piperazine.

The following examples illustrate the present invention:

EXAMPLE 1

Serinol (=1,3-dihydroxy-isopropylamine)

A. 1,3-dimethoxy-isopropanol

Sodium hydroxide (5.7 kg) is dissolved in 65 kg of boiling methanol. The boiling solution is stirred and treated within on hour with 12.5 kg of epichlorohydrin, the heat of reaction released keeping the reaction mixture at the boil. Boiling is continued for a further 6 hours under reflux. The mixture is now cooled to room temperature, its pH is adjusted to 7 by the addition of concentrated hydrochloric acid, the sodium chloride, which has precipitated, is filtered off and the filtrate is subjected to a fractional distillation under vacuum. By so doing, 14.77 kg of 1,3-dimethyl-isopropanol, boiling in the range of 63°–72° C. at 14 torr, are obtained. This yield corresponds to 91% of the theoretical.

B. 1,3-dimethoxy-isopropyl chloride

A mixture of 12 kg of 1,3-dimethoxy-isopropanol, 50 kg of chloroform and 160 g of pyridine is carefully treated at 55°–60° C. with 14.3 kg of thionyl chloride. The reaction solution is refluxed for 20 hours, until the evolution of gas (HCl and SO$_2$) has ceased completely.

The reaction solution now is fractionally distilled. 1,3-dimethoxy-isopropyl chloride, boiling in the range of 50°–55° C./torr, is obtained in a yield of 12.47 kg, corresponding to 90% of the theoretical.

C. 1,3-dimethoxy-isopropylamine 1,3-dimethyoxy-isopropyl chloride (1.3 kg) in 12.8 kg of 25% aqueous ammonia is heated for 2 hours in an autoclave at 170° C. The excess ammonia largely is evaporated off. The aqueous solution is treated with solid sodium hydroxide. The 1,3-dimethoxy-isopropylamine is extracted with methylene chloride.

The extract is freed from solvent and distilled under vacuum. 1,3-dimethoxy-isopropylamine, boiling in the range of 47°–49° C. at 14 torr or at 145° C. at 760 torr, is obtained in a yield of 894.3 g, corresponding to 80% of the theoretical. This compound is miscible with water and with organic solvent.

D. 1,3-dihydroxy-isopropylamine (=serinol)

Aqueous 35% hydrochloric acid (6.6 kg) is allowed to flow into 3.57 kg of 1,3-dimethoxy-isopropylamine (30 moles). A solution of 1,3-dimethoxy-isopropylamine hydrochloride in about 20–21% hydrochloric acid is formed. This reaction solution is heated to boiling under reflux conditions (bath temperature ca. 150° C.). The ether commences to splitt off, and methyl chloride which escapes through the condenser is formed with consumption of hydrochloric acid. The loss of hydrogen chloride is compensated for by constantly introducing hydrogen chloride gas in such a manner that a minimal flow of hydrogen chloride is barely detectable at the head of the reflux condenser. Thus, the concentration of the boiling hydrochloric acid constantly remains approximately in the azeotropic range. As a consequence of such a procedure, the ether splitting proceeds rapidly and is completed after refluxing for 30 hours. The reaction solution is now evaporated under vacuum. The oily residue is worked up either to serinol hydrochloride or to the free serinol base.

Serinol Hydrochloride

The above oily residue is taken up in 5 l of water, treated with a little activated charcoal, filtered and evaporated completely under vacuum. The residue is dissolved in 4 l of boiling 96% ethanol. On cooling and after seeding with crystals of 1,3-dihydroxy-isopropylamine hydrochloride, produced by rubbing a sample with a glass rod, almost complete crystallization of the serinol hydrochloride takes place within the course of 2 hours at the temperature of ice. The product is filtered off and dried.

Yield: 3.45 kg of serinol hydrochloride (=1,3-dihydroxy-isopropylamine hydrochloride), that is, 90% of the theoretical yield.

Melting point: 104°–105° C.

Purity: 99.8% (determined by titration with silver nitrate).

Thin layer chromatogram (TLC) on silica gel with a solvent of chloroform/methanol/concentrated ammonia=6:3:1. $R_f$=0.45.

Serinol Base

The oily residue from the evaporation, which was obtained after the ether splitting, is taken up in about 10 l of water and the chloride content is determined. Subsequently, an amount of 30% aqueous sodium hydroxide, exactly equivalent to the chloride content (about 4.5 kg) is added. The reaction material obtained is evaporated completely with stirring under vacuum. In so doing, the sodium chloride formed is suspended in the molten serinol base. The residue is taken up in ethanol, the sodium chloride is filtered off and washed with ethanol. The filtrate is evaporated under normal pressure, the ethanol being recovered. The residue from the evaporation, which contains the serinol, is distilled under a medium-high vacuum. Serinol (1,3-dihydroxy-isopropylamine), boiling in the range of 130°–140° C. at 0.1 torr, is obtained in a yield of 2.56 kg, corresponding to 92.6% of the theoretical based on the 1,3-dimethoxy-isopropylamine.

Melting point: 55°–56° C.

TLC on silica gel with a solvent of chloroform/methanol/conc. ammonia=6:3:1 $R_f$=0.25.

E. 1,3-dihydroxy-isopropylamine by hydrolysis of 1,3-dimethoxy-isopropylamine with hydrobromic acid 1,3-dimethoxy-isopropylamine (59.5 g) is added to 950 g of a 47% aqueous solution of hydrobromic acid. The reaction solution is refluxed for 5 hours and subsequently evaporated to dryness. The residue is dissolved in water, the solution decolorized with activated charcoal and allowed to percolate through a column filled with a strongly acidic cationic exchange resin (e.g. 500 ml of Amberlite® IR-120). The bromide-containing eluate is discarded. The serinol is dissolved from the ion-exchange resin with 2N ammonia. The basic solution is evaporated and the residue distilled under vacuum.

Serinol, boiling in the range of 117°–122° C. at 0.05 torr, is obtained in a yield of 38.7 g, corresponding to 85% of the theoretical.

TLC with a solvent of dioxane/conc. ammonia/water=6:1:2. $R_f$=0.55.

EXAMPLE 2

1,3-dihydroxy-2-methylamino-propane

A. 1,3-dimethoxy-2-methylamino-propane 1,3-dimethoxy-isopropyl chloride (222 g) in 1000 g of a 40% aqueous solution of methylamine is heated in an autoclave for 2 hours at 170° C. The reaction solution is evaporated and the residue is treated with ca. 80 g of solid sodium hydroxide. The organic phase, which is formed, is extracted with diethyl ether. The extract is freed from solvent and subsequently distilled under vacuum.

1,3-dimethoxy-2-methylamino-propane, boiling at 48° C. at 11–12 torr, is obtained in a yield of 179 g, corresponding to 84% of the theoretical.

Equivalent weight: calc. 133.19; found 133.71 (titrated with 0.1N perchloric acid).

Thin layer chromatogram (TLC) on silica gel with a solvent of chloroform/methanol/ammonia (15%)=85:14:1, one spot at $R_f$=0.70.

B. 1,3-dihydroxy-2-methylamino-propane 1,3-dimethoxy-2-methylamino-propane in 1000 ml of 20% hydrochloric acid is refluxed for 56 hours until, on the basis of periodic checks by means of thin layer chromatography, it can be shown that all of the starting material has disappeared and a largely uniform product has been formed. The reaction solution is evaporated to dryness. The residue is dissolved in 100 ml of water and added to a strongly acidic cationic resin (e.g. Amberlite® IR-120). The ion-exchange resin is washed with water until free from chloride. The product is now eluted from the resin with 2000 ml of 2N ammonia. The eluate is evaporated. The residue is fractionally distilled under vacuum.

Two fractions are obtained:

1. Boiling point 80°–81° C. at 1 torr. Equivalent weight found=120
2. Boiling point 80°–82° C. at 0.1 torr. Equivalent weight found=105.7

The first fraction of 3.9 g, corresponding to 6.5% of the theoretical, consists of 1-methoxy-3-hydroxy-2-methylamino-propane (equivalent weight calc. 119.17).

The second fraction of 42 g, corresponding to 80% of the theoretical, consists of 1,3-dihydroxy-2-methylamino-propane (equivalent weight calc. 105.1).

TLC on silica gel with a solvent of methylene chloride/methanol/conc. ammoni=6:3:1.

1,3-dihydroxy-2-methylamino-propane: $R_f$=0.46.

1-methoxy-3-hydroxy-2-methylamino-propane: $R_f$=0.91.

The picrate of 1,3-dihydroxy-2-methylamino-propane, after recrystallization from ethanol, melts at 104°–105° C.

EXAMPLE 3

1,3-dihydroxy-2-ethylamino-propane

A. 1,3-diethoxy-isopropyl chloride

This compound is obtained as in Example 1A/B by reacting epichlorohydrin with ethanol in the presence of potassium hydroxide to form 1,3-diethoxy-isopropanol (boiling point 190° C. at 760 torr or 85° C. at 12 torr) and treating this with thionyl chloride at the boil and in the presence of a little pyridine.

Boiling point: 62° C. at 14 torr.

B. 1,3-diethoxy-2-ethylamino-propane 1,3-diethoxy-isopropyl chloride (83.4 g) in 200 ml of 70% aqueous ethylamine is heated for 2 to 4 hours in an autoclave at 175° C. The reaction mixture is worked up as described in Example 2A. 1,3-diethoxy-2-ethylamino-propane with a boiling point of 65° C. at 14 torr is obtained in a yield of 70 g, corresponding to 80% of the theoretical.

C. 1,3-dihydroxy-2-ethylamino-propane 1,3-diethoxy-2-ethylamino-propane (52.6 g) is added to 900 g of 47% hydrobromic acid. The reaction solution is refluxed for 7–9 hours and worked up as in Example 1 E. 1,3-dihydroxy-2-ethylamino-propane, with a boiling point of 88° C. at 0.2 torr, is obtained in a yield of 28.3 g, corresponding to 79% of the theoretical. This compound is readily soluble in water.

EXAMPLE 4

1,3-dihydroxy-2-dimethylamino-propane

A. 1,3-dimethoxy-2-dimethylamino-propane 1,3-dimethoxy-isopropyl chloride (111 g) in 350 g of 40% aqueous dimethylamine is heated in an autoclave for 2–4 hours at 170° C. The product is worked up by the method described in Example 2A. 1,3-dimethoxy-2-dimethylamino-propane, boiling in the range of 50° to 53° C. at 12 to 14 torr, is obtained in a yield of 85% of the theoretical.

B. 1,3-dihydroxy-2-dimethylamino-propane 1,3-dimethoxy-2-dimethylamino-propane (100 g) in 1000 ml of 20% hydrochloric acid is refluxed for 70 hours and then worked up as described in Example 2. 1,3-dihydroxy-2-dimethylamino-propane, with a boiling point of 90°–92° C. at 0.6 torr, is obtained in a yield of 69.64 g, corresponding to 86% of the theoretical.

EXAMPLE 5

1,3-dihydroxy-2-diethylamino-propane

This compound is obtained in a similar manner by heating 69.3 g of 1,3-dimethoxy-isopropyl chloride with 110 g of diethylamine in an autoclave and hydrolyzing the 1,3-dimethoxy-2-diethylamino-propane obtained (boiling point 65° C. at 16 torr) by boiling it with azeotropic, aqueous hydrochloric acid.

Boiling point: 115° C. at 0.4 torr. This compound is very readily soluble in water.

EXAMPLE 6

1,3-dihydroxy-2-(2'-hydroxyethyl)-amino-propane

A. 1,3-dimethoxy-2-(2'-hydroxyethyl)-amino-propane 1,3-dimethoxy-isopropyl chloride (138.6 g, 1 mole) is mixed with 250 g of 2-aminoethanol and heated for some hours at 160°–165° C. The unreacted, excess 2-aminoethanol is distilled off under vacuum through a column. The residue from the evaporation is treated with solid sodium hydroxide and the product extracted repeatedly with diethyl ether. The extract is evaporated and the residue is distilled under vacuum.

1,3-dimethoxy-2-(2'-hydroxyethyl)-amino-propane with a boiling point of 124°–126° C. at 11 torr, is obtained in a yield of 148.5 g, corresponding to 91% of the theoretical.

Equivalent weight: calc. 163.2, found 163.9 (titrated with 0.1N perchloric acid).

TLC on silica gel with a solvent of chloroform/methanol/ammonia (25%)=85:14:1. One spot, $R_f$=0.45.

B. 1,3-dihydroxy-2-(2'-hydroxyethyl)-amino-propane 1,3-dimethoxy-2-(2'-hydroxyethyl)-amino-propane (81.6 g) in 1000 ml of 20% hydrochloric acid is refluxed for 65 hours until the spot of starting material has disappeared in the TLC and a uniform new product has been formed. This is worked up as described in Examples 1D or 2B. 1,3-dihydroxy-2-(2'-hydroxyethyl)-amino-propane, boiling in the range of 138°–140° C. at 0.05 torr, is obtained in a yield of 59.5 g, corresponding to 88% of the theoretical.

Equivalent weight: calc. 135.17; found 135.86.

TLC on silica gel with a solvent of methylene chloride/methanol/conc. ammonia=6:3:1; $R_f$=0.49.

The picrate of 1,3-dihydroxy-2-(2'-dihydroxyethyl)-amino-propane melts at 103°–104° C.

EXAMPLE 7

1(N)-(1,3-dimethoxy-isopropyl)-piperazine

A. 1(N)-(1,3-dimethoxy-isopropyl)-piperazine 1,3-dimethoxy-isopropyl chloride (138.6 g) is mixed with 430 g of piperazine, fused and stirred for 4 to 6 hours at 140°–145° C. After cooling, the phases are separated. The lighter phase is freed from excess piperazine by distillation under vacuum. The residue from the distillation is filtered and washed with diethyl ether. The filtrate is evaporated and the residue is vacuum distilled. 1(N)-(1,3-dimethoxy-isopropyl)-piperazine, boiling at 121°–124° C. at 11 torr, is obtained in a yield of 152.5 g, corresponding to 81% of the theoretical.

Equivalent weight: calc. 94.14; found 93.75.

TLC on silica gel with a solvent of isobutanol/isopropanol/ammonia (25%)=35:35:30. One spot with $R_f$=0.67.

B. 1(N)-(1,3-dihydroxyisopropyl)-piperazine

1(N)-(1,3-dimethoxy-isopropyl)-piperazine (65.9 g) in 740 ml of 20% hydrochloric acid is refluxed for 65 hours. The product is worked up as described in Examples 1 D or 2 B. On distillation, two fractions are obtained:

1. Boiling point of 100° C. at 0.5 torr. Equivalent weight: 87.72; amount 6.1 g.
2. Boiling point of 125° C. at 0.05 torr. Equivalent weight 80.31; amount 41 g.

Both products crystallize on being allowed to stand. The first fraction consists of 1(N)-(1-methoxy-3-hydroxy-isopropyl)-piperazine (equivalent weight calc. 87.13), yield: 10%; melting point: ca. 50° C.

The second fraction consists of 1(N)-(1,3-dihydroxy-isopropyl)-piperazine (equivalent weight calc.: 80.11); yield: 73% of the theoretical.

Melting point (after recrystallization from isopropanol): 113°–115° C.

TLC on silica gel with a solvent of methylene chloride/methanol/conc. ammonia=6:3:1.

$R_f$ (first fraction): 0.79.

$R_f$ (second fraction): 0.45.

EXAMPLE 8

4(N)-(1,3-dihydroxy-isopropyl)-morpholine

A. 4(N)-(1,3-dimethoxy-isopropyl)-morpholine 1,3-dimethoxy-isopropyl-chloride (69.3 g, 0.5 moles) is mixed with 87 g (1 mole) of morpholine and heated for several hours to ca. 160°–165° C. By extracting the reaction mixture with isopropanol, the product is separated from morpholine hydrochloride. Subsequently, it is distilled under vacuum.

Yield: 76 g, corresponding to 80% of the theoretical.

B. 4(N)-(1,3-dihydroxy-isopropyl)-morpholine

4(N)-(1,3-dimethoxy-isopropyl)-morpholine in 900 ml of 20% hydrochloric acid is refluxed for about 70 hours and subsequently worked up as described in Example 7. 4(N)-(1,3-dihydroxy-isopropyl)-morpholine with a boiling point of 120° C. at 0.15 torr, is obtained in a yield of 48.4 g, corresponding to 75% of the theoretical.

EXAMPLE 9

1(N)-(1,3-dihydroxy-isopropyl)-piperidine

A. 1(N)-(1,3-dimethoxy-isopropyl)-piperidine 1,3-dimethoxy-isopropyl chloride (69.3 g, 0.5 moles) is mixed with 85 g of piperidine (1 mole), heated in a bomb for several hours at 170° C. and subsequently worked up as described in Example 8.

Yield: 71.14 g, corresponding to 76% of the theoretical.

B. 1(N)-(1,3-dihydroxy-isopropyl)-piperidine

1(N)-(1,3-dimethoxy-isopropyl)-piperidine (70.2 g, 0.375 moles) in 850 ml of 20% hydrochloric acid is refluxed for 70 hours and subsequently worked up as described in the preceding examples. 1(N)-(1,3-dihydroxy-isopropyl)-piperidine, with a boiling point of 125° C. at 1-2 torr, is obtained in a yield of 50.75 g, corresponding to 85% of the theoretical.

EXAMPLE 10

1(N)-(1,3-dihydroxy-isopropyl)-pyrrolidine

This compound is obtained in a similar manner by heating 69.3 g of 1,3-dimethoxy-isopropyl chloride with 71.1 g of pyrrolidine in a bomb and hydrolyzing the 1(N)-(1,3-dimethoxy-isopropyl)-pyrrolidine obtained by boiling it with 20% aqueous hydrochloric acid.

Boiling point: 120° C. at 2-4 torr. The compound is water soluble.

EXAMPLE 11

1,3-dihydroxy-2-(2',3'-dihydroxypropyl)-amino-propane

A. 1,3-dimethoxy-2-(2',3'-dihydroxypropyl)-amino-propane 1,3-dimethoxy-isopropyl chloride (138.6 g, 1 mole) is heated with 2,3-dihydroxypropylamine (182.2 g, 2 moles) for several hours at 160°-165° C. The residue is partitioned between chloroform and water. The chloroform solution is evaporated. The residue from the evaporation consists of 170 g of 1,3-dimethoxy-2-(2',3'-dihydroxypropyl)-amino-propane, corresponding to 88% of the theoretical.

B. 1,3-dihydroxy-2-(2',3'-dihydroxypropyl)-amino-propane 1,3-dimethoxy-2-(2',3'-dihydroxypropyl)-amino-propane (96.6 g, 0.5 moles) in 1000 ml of 20% hydrochloric acid is refluxed for 65 hours and subsequently worked up according to the method described in Example 2 B. The readily water soluble 1,3-dihydroxy-2-(2',3'-dihydroxypropyl)-amino-propane, which boils at about 155° C. at 0.05 torr, is obtained in a yield of 64.4 g, corresponding to 78% of the theoretical.

EXAMPLE 12

N,N-bis-(1,3-dihydroxy-isopropyl)-amine

This compound is obtained as described in Example 11 by heating 1,3-dimethoxy-isopropyl chloride (69.3 g) with serinol (91.1 g) and hydrolyzing the so obtained 1,3-dimethoxy-2-(1',3'-dihydroxy-isopropyl)-amino-propane (82 g) by boiling with 20% hydrochloric acid (1000 ml). N,N-bis-(1,3-dihydroxy-isopropyl)-amine boils at about 150° C. at 0.05 torr and is very readily soluble in water.

EXAMPLE 13

1,3-dihydroxy-2-[N-methyl-N-(2',3',4',5'-tetrahydroxypentyl)]-amino-propane

By heating 69.3 g (0.5 moles of 1,3-dimethoxy-isopropyl chloride with 165.2 g (1.0 mole) of N-methyl-d-xylamine (=1 methylamino-1-desoxy-d-xylitol (Dorn et al, Chem. Ber. 99, 812, 1966) for several hours at 160°-170° C., 1,3-dimethoxy-2-[N-methyl-N-(2',3',4',5'-tetrahydroxy-pentyl)]-amino-propane is obtained.

This ether is hydrolyzed to 1,3-dihydroxy-2-[N-methyl-N-(2',3',4',5'-tetrahydroxy-pentyl)]-amino-propane, as described in Examples 6 and 11, by refluxing with 20% hydrochloric acid. The new compound forms deliquescent, colorless crystals, which eagerly take up carbon dioxide and, in so doing, are partially converted into the carbonate. This compound is very readily soluble in water.

EXAMPLE 14

1,3-dihydroxy-2-[N-methyl-N-N-(2',3',4',5',6'-pentahydroxyhexyl)]-amino-propane 1,3-dimethoxy-isopropyl chloride (69.3 g, 0.5 moles) and 195.3 g of N-methyl-d-glucamine (=1-deoxyl-1-methylamino-d-glucitol) (1 mole) is heated for 3 hours at 170° C. The desired intermediate can be separated by boiling it with ethanol or isopropanol from the difficultly soluble N-methyl-d-glucamine hydrochloride, which is formed in the reaction.

1,3-dimethoxy-2-[N-methyl-N-(2',3',4',5',6'-pentahydroxy-hexyl)]-amino-propane is split by refluxing it with 20% hydrochloric acid to 1,3-dihydroxy-2-[N-methyl-N-(2',3',4',5',6'-pentahydroxyhexyl)]-amino-propane. This new compound is a strong base which is readily soluble in water and bonds carbon dioxide from the air. In so doing, it is partially converted into the carbonate. It forms colorless crystals which melt at about 130° C.

What is claimed is:

1. The method for the synthesis of serinol comprising reacting 1,3-dimethoxy-isopropylchloride intially with excess ammonia by heating to 170° C. to form 1,3-dimethoxy-isopropylamine and subsequently converting this intermediate to serinol by refluxing it with aqueous hydrochloric acid and wherein the hydrogen chloride consumed is constantly or is periodically replaced in order to accelerate the reaction.

2. A method for splitting off the ether groups from 1,3-dimethoxy-isopropylamine comprising heating the 1,3-dimethoxy-isopropylamine with aqueous hydrochloric acid.

* * * * *